United States Patent [19]
Segal

[11] Patent Number: 6,033,431
[45] Date of Patent: *Mar. 7, 2000

[54] DIODE LASER IRRADIATION SYSTEM FOR BIOLOGICAL TISSUE STIMULATION

[76] Inventor: Kim Robin Segal, 18902 White Water La., Dallas, Tex. 75287

[ * ] Notice: This patent is subject to a terminal disclaimer.

[21] Appl. No.: 09/034,125

[22] Filed: Mar. 3, 1998

Related U.S. Application Data

[63] Continuation-in-part of application No. 08/621,950, Mar. 25, 1996, Pat. No. 5,755,752, which is a continuation-in-part of application No. 07/873,385, Apr. 24, 1992, abandoned.

[51] Int. Cl.$^7$ .............................. A61N 7/00; A61B 17/36
[52] U.S. Cl. .................................. 607/89; 607/90; 606/3; 606/10; 606/13
[58] Field of Search ................................... 606/2, 10, 11, 606/12, 13, 14, 16, 15; 607/88, 89

[56] References Cited

U.S. PATENT DOCUMENTS

| | | |
|---|---|---|
| 3,769,963 | 11/1973 | Goldman et al. . |
| 3,900,034 | 8/1975 | Katz et al. . |
| 4,158,207 | 6/1979 | Bishop et al. . |
| 4,173,317 | 5/1979 | Ljung et al. . |
| 4,573,465 | 3/1986 | Sugiyama et al. . |
| 4,573,467 | 3/1986 | Rich et al. . |
| 4,628,513 | 12/1986 | White . |
| 4,792,959 | 12/1988 | Mueller et al. . |
| 4,852,567 | 8/1989 | Sinofsky ..................................... 606/16 |
| 4,930,504 | 6/1990 | Diamantopoulos et al. . |
| 4,984,242 | 1/1991 | Scifres et al. . |
| 5,049,147 | 9/1991 | Danon . |
| 5,050,597 | 9/1991 | Daikuzono . |
| 5,082,799 | 1/1992 | Holmstrom et al. . |
| 5,086,432 | 2/1992 | Esterowitz et al. . |
| 5,107,509 | 4/1992 | Esterowitz et al. . |
| 5,150,704 | 9/1992 | Tatebayashi et al. . |
| 5,200,966 | 4/1993 | Esterowitz et al. . |
| 5,222,091 | 6/1993 | Holmstrom et al. . |
| 5,259,380 | 11/1993 | Mendes et al. .............................. 606/9 |
| 5,358,503 | 10/1994 | Bertwell et al. ............................. 606/9 |
| 5,409,482 | 4/1995 | Diamantopoulos . |
| 5,445,146 | 8/1995 | Bellinger . |
| 5,468,238 | 11/1995 | Mersch ...................................... 606/15 |
| 5,514,126 | 5/1996 | Prescott ..................................... 606/10 |
| 5,616,140 | 4/1997 | Prescott ..................................... 606/10 |
| 5,693,041 | 12/1997 | Murphy-Chutorian ..................... 606/2 |
| 5,755,752 | 5/1998 | Segal ........................................ 607/89 |

*Primary Examiner*—Linda C. M. Dvorak
*Assistant Examiner*—Sonya Harris-Ogugua
*Attorney, Agent, or Firm*—Haynes and Boone, LLP

[57] ABSTRACT

A diode laser irradiation system for treating biological tissue of a subject without exposing the tissue to damaging thermal effects. The system includes a manipulable wand for contact with the tissue, a diode laser disposed in the wand for irradiating the tissue with coherent optical energy at a power output level of less than one thousand milliwatts, and laser setting controls for operating the diode laser to achieve a rate of absorption and conversion to heat in the irradiated tissue in a range between a minimum rate sufficient to elevate the average temperature of the irradiated tissue to a level above the basal body temperature of the subject, and a maximum rate which is less than the rate at which the irradiated tissue is converted into a collagenous.

3 Claims, 2 Drawing Sheets

DIODE LASER IRRADIATION SYSTEM FOR BIOLOGICAL TISSUE STIMULATION

CROSS REFERENCE TO RELATED APPLICATION

This is a continuation of U.S. Ser. No. 08/621,950, filed Mar. 25, 1996, U.S. Pat. No. 5,755,752, which is a continuation-in-part of U.S. Ser. No. 07/873,385, filed on Apr. 24, 1992, abandoned.

BACKGROUND OF THE INVENTION

The present invention relates generally to the treatment of living biological tissue by optical irradiation, and in particular to a system for stimulating soft, living tissue by diode laser irradiation.

Various non-surgical means have been employed in the therapeutic treatment of living tissue. Such techniques have included the application of ultrasonic energy, electrical stimulation, high frequency stimulation by diathermy, X-rays and microwave irradiation. While these techniques have shown some therapeutic benefit, their use has been somewhat limited because they generate excessive thermal energy which can damage tissue. Consequently, the energy levels associated with therapeutic treatments involving diathermy, X-ray, microwave and electrical stimulation have been limited to such low levels that little or no benefit has been obtained. Moreover, the dosage or exposure to microwaves and X-ray radiation must be carefully controlled to avoid causing health problems related to the radiation they generate. Ultrasonic energy is non-preferentially absorbed and affects all of the tissue surrounding the area to which it is directed.

Optical energy generated by lasers has been used for various medical and surgical purposes because laser light, as a result of its monochromatic and coherent nature, can be selectively absorbed by living tissue. The absorption of the optical energy from laser light depends upon certain characteristics of the wavelength of the light and properties of the irradiated tissue, including reflectivity, absorption coefficient, scattering coefficient, thermal conductivity, and thermal diffusion constant. The reflectivity, absorption coefficient, and scattering coefficient are dependent upon the wavelength of the optical radiation. The absorption coefficient is known to depend upon such factors as interband transition, free electron absorption, grid absorption (photon absorption), and impurity absorption, which are also dependent upon the wavelength of the optical radiation.

In living tissue, water is a predominant component and has, in the infrared portion of the electromagnetic spectrum, an absorption band determined by the vibration of water molecules. In the visible portion of the spectrum, there exists absorption due to the presence of hemoglobin. Further, the scattering coefficient in living tissue is a dominant factor.

Thus, for a given tissue type, the laser light may propagate through the tissue substantially unattenuated, or may be almost entirely absorbed. The extent to which the tissue is heated and ultimately destroyed depends on the extent to which it absorbs the optical energy. It is generally preferred that the laser light be essentially transmissive through tissues which are not to be affected, and absorbed by tissues which are to be affected. For example, when applying laser radiation to a region of tissue permeated with water or blood, it is desired that the optical energy not be absorbed by the water or blood, thereby permitting the laser energy to be directed specifically to the tissue to be treated. Another advantage of laser treatment is that the optical energy can be delivered to the treatment tissues in a precise, well defined location and at predetermined, limited energy levels.

Ruby and argon lasers are known to emit optical energy in the visible portion of the electromagnetic spectrum, and have been used successfully in the field of ophthalmology to reattach retinas to the underlying choroidea and to treat glaucoma by perforating anterior portions of the eye to relieve interoccular pressure. The ruby laser energy has a wavelength of 694 nanometers (nm) and is in the red portion of the visible spectrum. The argon laser emits energy at 488 nm and 515 nm and thus appears in the blue-green portion of the visible spectrum. The ruby and argon laser beams are minimally absorbed by water, but are intensely absorbed by blood chromogen hemoglobin. Thus, the ruby and argon laser energy is poorly absorbed by non-pigmented tissue such as the cornea, lens and vitreous humor of the eye, but is absorbed very well by the pigmented retina where it can then exert a thermal effect.

Another type of laser which has been adapted for surgical use is the carbon dioxide ($CO_2$) gas laser which emits an optical beam which is absorbed very well by water. The wavelength of the $CO_2$ laser is 10,600 nm and therefore lies in the invisible, far infrared region of the electromagnetic spectrum, and is absorbed independently of tissue color by all soft tissues having a high water content. Thus, the $CO_2$ laser makes an excellent surgical scalpel and vaporizer. Since it is completely absorbed, its depth of penetration is shallow and can be precisely controlled with respect to the surface of the tissue being treated. The $CO_2$ laser is thus well-suited for use in various surgical procedures in which it is necessary to vaporize or coagulate neutral tissue with minimal thermal damage to nearby tissues.

Another laser in widespread use is the neodymium doped yttrium-aluminum-garnet (Nd:YAG) laser. The Nd:YAG laser has a predominant mode of operation at a wavelength of 1064 nm in the near infrared region of the electromagnetic spectrum. The Nd:YAG optical emission is absorbed to a greater extent by blood than by water making it useful for coagulating large, bleeding vessels. The Nd:YAG laser has been transmitted through endoscopes for treatment of a variety of gastrointestinal bleeding lesions, such as esophageal varices, peptic ulcers, and arteriovenous anomalies.

The foregoing applications of laser energy are thus well-suited for use as a surgical scalpel and in situations where high energy thermal effects are desired, such as tissue vaporization, tissue cauterization, and coagulation.

Although the foregoing laser systems perform well, they commonly generate large quantities of heat and require a number of lenses and mirrors to properly direct the laser light and, accordingly, are relatively large, unwieldy, and expensive. These problems are somewhat alleviated in some systems by locating a source of laser light distal from a region of tissue to be treated and providing fiber optic cable for carrying light generated from the source to the tissue region, thereby obviating the need for a laser light source proximal to the tissue region. Such systems, however, are still relatively large and unwieldy and, furthermore, are much more expensive to manufacture than a system which does not utilize fiber optic cable. Moreover, the foregoing systems generate thermal effects which can damage living tissue, rather then provide therapeutic treatment to the tissue.

Therefore, what is needed is a system and method for economically stimulating soft, living tissue with laser energy without damaging the tissue from the thermal effects of the laser energy.

SUMMARY OF THE INVENTION

The present invention, accordingly, provides a system and a method that retains all of the advantages of the foregoing systems while reducing the size and cost of the system. To this end, a system for treating biological tissue without exposing the tissue to damaging thermal effects, comprises a wand which houses an Indium Gallium Arsenide (In:GaAs) diode laser configured for generating coherent optical energy radiation having a wavelength in the range of the near infrared region of the electromagnetic spectrum at a power output in the range of from about 100 milliwatts (mw) to about 1000 mw. The coherent optical energy radiation is focused on the treatment area to achieve a rate of absorption and conversion to heat in the irradiated tissue in the range between a minimum rate sufficient to elevate the average temperature of the irradiated tissue to a level above the basal body temperature of the living subject, and a maximum rate which is less than the rate at which the irradiated tissue is converted into a collagenous substance.

In another aspect of the present invention, the amount of Indium with which the Gallium Arsenide in the diode is doped is appropriate to cause the wavelength of laser light generated by the diode to be in a range between 1064±20 nm and 2500±20 nm.

The system and method additionally enable the treatment time, the power generated by the laser, and the mode of operation (pulsed or continuous wattage (CW)) to be carefully controlled by an operator according to a desired treatment protocol.

An advantage achieved with the present invention is that it enables laser light to be safely and effectively applied to a region of living tissue for therapeutic purposes, for example, to reduce pain, reduce inflammation, and enhance the healing of tissue by stimulation of microcirculation, without exposing the tissue to damaging thermal effects.

Another advantage of the present invention is that, because the laser light is generated within the wand, it is less expensive to manufacture than systems utilizing fiber optic cables.

Another advantage of the present invention is that it provides for high power dissipation levels ranging from about 500 milliwatts (mw) to about 1000 mw in both continuous wattage (CW) or pulsed modes of operation. The diode laser system enables such high power dissipation levels to be achieved utilizing a portable, battery operated arrangement.

DETAILED DESCRIPTION OF THE PREFERRED EMBODIMENT

Figure 1:
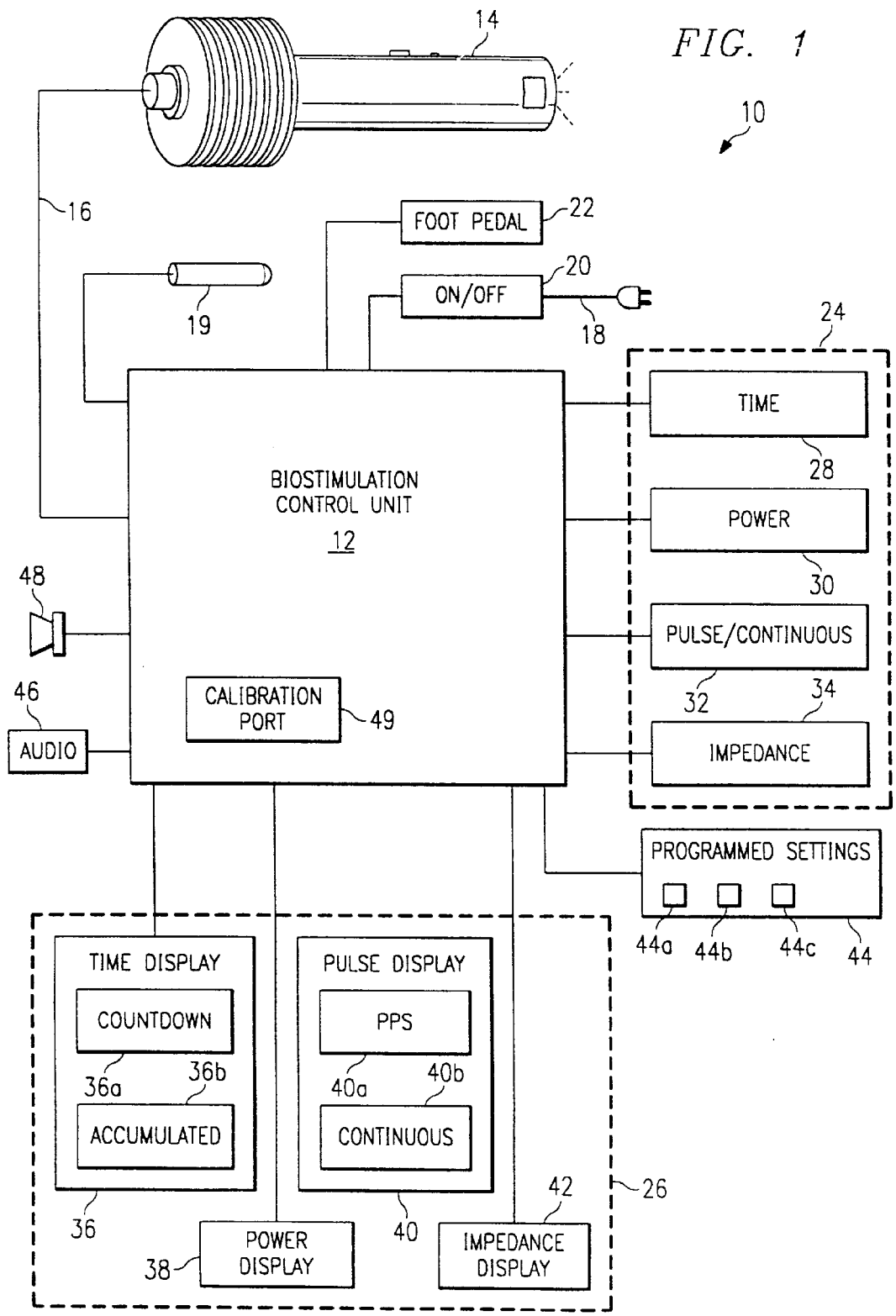
FIG. 1 shows a schematic diagram of a diode laser irradiation system of the present invention.

Referring to FIG. 1, the reference numeral 10 refers generally to the diode laser irradiation system of the present invention which includes a biostimulation control unit 12 for controlling the operation of a hand-operated probe, i.e., a laser treatment wand 14, electrically connected to the control unit via a coaxial cable 16. As will be described in detail below, the wand 14 houses a diode laser capable of emitting low level reactive laser light for use in tissue irradiation therapy.

The control unit 12 receives power through a power supply line 18 adapted for connection to a conventional 120-volt power outlet. A ground piece 19 is connected to the control unit 12 and is held by a patient receiving the tissue irradiation therapy to provide an electrical ground for safety purposes. An on/off switch 20 is connected in series with the line 18 for controlling the flow of power through the line. A foot pedal 22 is connected to the control unit 12 and is depressible for activating the generation and emission of laser light from the wand 14. Activation may alternatively, or additionally, be provided using a switch on the wand 14.

The control unit 12 includes laser setting controls 24 and corresponding setting displays 26. The setting controls 24 are utilized to select operational parameters of the control unit 12 to effect the rate of absorption and conversion to heat of tissue irradiated by the wand 14, according to desired treatment protocols. Generally, the treatment protocols provide for a rate of absorption and conversion to heat in the irradiated tissue in a range between a minimum rate sufficient to elevate the average temperature of the irradiated tissue to a level above the basal body temperature of the subject and a maximum rate which is less than the rate at which the irradiated tissue is converted to a collagenous substance. The treatment protocols vary time, power, and pulse/continuous mode parameters in order to achieve the desired therapeutic effects.

The setting controls 24 include a treatment time control 28, a power control 30, and a pulse/continuous mode control 32. Adjustments in treatment time, power and pulse/continuous mode operation of the wand 14 utilizing the controls 28–32 make possible improved therapeutic effects based upon the aforementioned treatment protocols involving one or more of these parameters. Also, an impedance control 34 is provided adjusting an impedance measurment of the tissue to a baseline value, according to skin resistance, as discussed further below, whereby improvements in tissue condition may be monitored. It is understood that, according to the specific embodiment of the control unit 12, the setting controls 24 may include any combination of one or more of the controls 28–34.

The setting displays 26 include a time display 36, a power display 38, a pulse display 40 and an impedance display 42. In one embodiment, each of the displays 26 are light emitting diode (LED) displays such that the corresponding setting controls 24 can be operated to increment or decrement the settings, which are then indicated on the displays. A programmed settings control 44 is used to save setting selections and then automatically recall them for convenience, using one or more buttons 44a–44c, for example.

The time control 28 adjusts the time that laser light is emitted from the wand 14 from 0.01 to 9.99 minutes in 0.01 minute intervals, as indicated on the time display 36. The time display 36 includes a countdown display 36a and an accumulated display 36b. Once the time control 28 is set, the countdown display 36a indicates the setting so that as the wand 14 is operated the time is decremented to zero. The accumulated time display 36b increments from zero (or any other reset value) as the wand 14 is operated so that the total treatment time is displayed. The time display 36 takes into account the pulsed or continuous mode operation of the system 10.

The power control 30 adjusts the power dissipation level of the laser light from the wand 14 in a range from zero to 1000 mw, with typical operation ranging from about 500 mw to 1000 mw. The pulse/continuous mode control 32 sets the system 10 to generate laser light energy from the wand 14 either continuously or as a series of pulses. The control 32 may include, for example, a pulse duration rheostat (not shown) for adjusting the pulse-on or pulse-off time of the wand 14. In one implementation, the pulses-per-second (PPS) is set in a range from zero to 9995, adjustable in 5 step increments. The PPS setting is displayed on a PPS display 40a. The pulse duration may alternatively, or additionally, be displayed indicating the duty cycle of pulses ranging from 5 to 99 (e.g., 5 meaning that the laser is "on" 5% of the time). A continous mode display 40b is activated when the system 10 is being operated in the continuous wattage (CW) mode of operation.

An audio volume control 46 is provided for generating an audible warning tone from a speaker 48 when laser light is being generated. Thus, for example, the tone may be pulsed when the system is operating in the pulse mode of operation.

The impedance control 34 is a sensitivity setting that is calibrated and set, according to the tissue skin resistance, to a baseline value which is then indicated on the impedance display 42. As therapy progresses the impedance readout on the display 42 changes (i.e., it decreases) thereby indicating progress of treatment.

A calibration port 49 is utilized to verify laser performance by placing the wand 14 in front of the port and operating the system 10. The port 49 determines whether the system 10 is operating within calibration specifications and automatically adjusts the system parameters.

While not shown, the control unit 12 includes digital and analog electronic circuitry for implementing the foregoing features. The details of the electronic circuitry necessary to implement these features will be readily understood by one of ordinary skill in the art in conjunction with the present disclosure and therefore will not be described in further detail.

Figure 2:
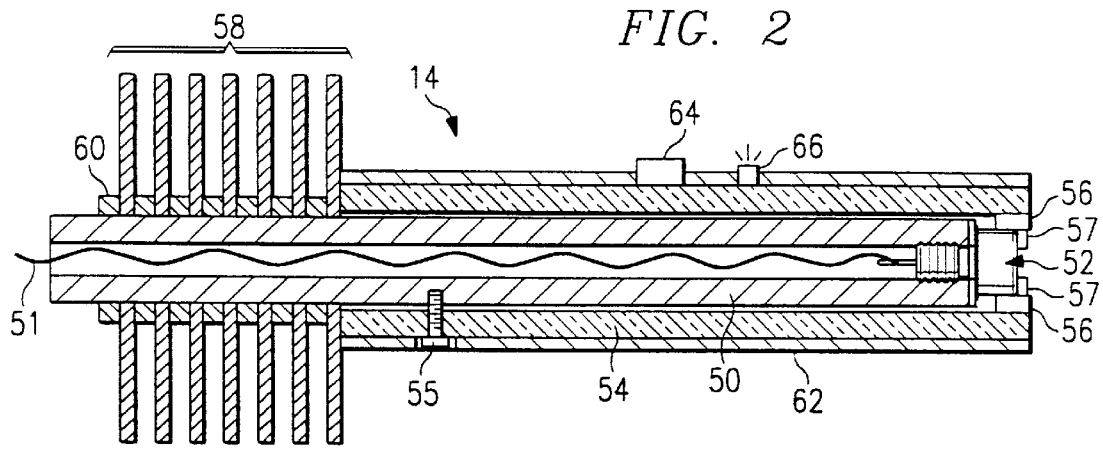
FIG. 2 shows an elevational view of a wand used in the system of FIG.

Referring to FIG. 2, the wand 14, sized to be easily manipulated by the user, includes a heat-conductive, metal bar 50. The bar 50 is hollow along its central axis and is threaded on its interior at a first end for receiving a laser resonator 52, described further below with reference to FIGS. 3A and 3B. Wiring 51 extends from the resonator 52 through the hollow axis of the bar 50 for connection to the coaxial cable 16 (FIG. 1). In the preferred embodiment the bar 50 is copper or steel and thus conducts electricity for providing a ground connection for the resonator 52 to the cable 16.

A glass noryl sleeve 54 is placed over the bar 50 for purposes of electrical and thermal insulation. A screw 55 extending through the sleeve 54 anchors the sleeve to the bar 50. As shown, the resonator 52 is recessed slightly within the sleeve 54. An impedance oring 56, formed of a conductive metal, is press-fitted into the end of the sleeve 54 so that when the wand 14 makes contact with tissue, the ring 56 touches the tissue. The ring 56 is electrically connected through the wand 14 to the unit 12. The ring 56 measures impedance by measuring angular DC resistance with an insulator ohmmeter, for example, of the tissue being irradiated by the wand 14 which is then displayed as impedance on the display 42. Any other suitable impedance measurement circuit may be utilized, as will be apparent to one skilled in the art. Measurements of impedance are useful in therapy to determine whether healing has occurred. For example, a baseline measurement of impedance provides an objective value of comparison wherein as the tissue heals, a lower impedance approaching the baseline is observed. The impedance value read can also be used to determine the amount of milliwattage and time of treatment appropriate for the patient.

A feedback sensor 57 is located in the end of the sleeve 54 for measuring the output of the resonator 52. While not shown, the sensor 57 is connected electronically to the control unit 12 and to a feedback circuit within the control unit. A small percentage of the diode laser light from the resonator 52 is thus detected by the sensor 57 and channeled into the feedback circuit of the control unit 12 to measure and control performance of the resonator. Out-of-specification temperature, power, pulse frequency or duration is thus corrected or the system 10 is automatically turned off.

Multiple metallic fins 58 are placed over the end of the bar 50 and are separated and held in place by spacers 60 press-fitted over the bar 50. The fins 58 act as a heat sink to absorb heat from the laser through the bar 50 and dissipate it into the surrounding air. The spacers 60 placed between each fin 58 enable air to flow between the fins, thereby providing for increased heat transfer from the wand 14.

A casing 62 fits over the sleeve 54 and serves as a hand grip and structure to support a switch 64 and light 66. The switch 64 is used to actuate the wand 14 by the operator wherein the switch must be depressed for the wand to operate. The switch 64 is wired in a suitable manner to the control unit 12 and is used either alone or in conjunction with the foot pedal 22. The light 66 is illuminated when the wand 14 is in operation.

Figure 3A:
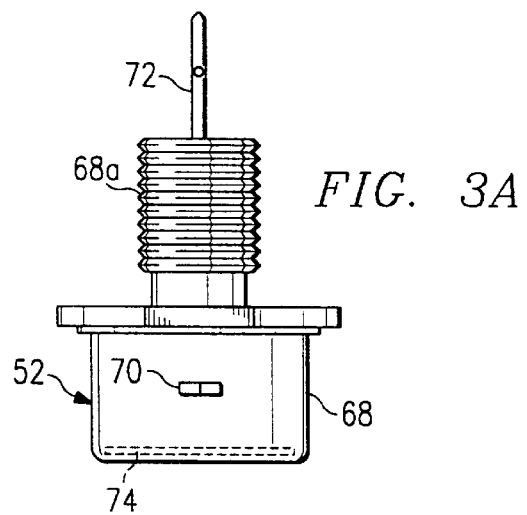
FIG. 3A shows an enlarged, elevational view of a laser resonator used in the wand of FIG. 2.

As shown in FIG. 3A, the laser resonator 52 includes a housing 68 having threads 68a configured for matingly engaging the threaded portion of the bar 50 in its first end. An Indium-doped Gallium Arsenide (In:GaAs) semiconductor diode 70 is centrally positioned in the housing 68 facing in a direction outwardly from the housing 68, and is electrically connected for receiving electric current through the threads 68a and an electrode 72 connected to the wiring 51 that extends longitudinally through the hollow interior of the tube 50 (FIG. 2). The amount of Indium with which the Gallium Arsenide is doped in the diode 70 is an amount appropriate so that the diode 70, when electrically activated, generates, in the direction outwardly from the housing 68, low level reactive laser light having, at a power output level of 100–1000 mw, a fundamental wavelength ranging from, depending upon the implementation, about 1064±20 nm to 2500±20 nm in the near-infrared region of the electromagnetic spectrum. Other types of diode semiconductor lasers may also be used to produce the foregoing wavelengths, e.g., Helium Neon, GaAs or the like.

Figure 3B:
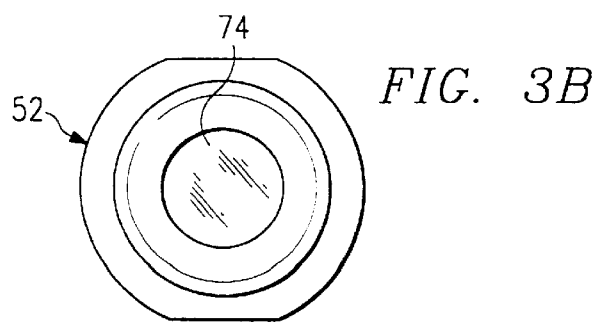
FIG. 3B shows an enlarged, end view of the laser resonator used in the wand of FIG. 3A.

As shown in FIGS. 3A and 3B, a lens 74 is positioned at one end of the housing 68 in the path of the generated laser light for focusing the light onto tissue treatment areas of, for example, 0.5 mm$^2$ to 2 mm$^2$, and to produce in the treatment areas an energy density in the range of from about 0.01 to about 0.15 joules/mm$^2$. The lens 74 may be adjusted to determine depth and area of absorption.

The operating characteristics of the diode 70 are an output power level of 100–1000 mw, a center fundamental wavelength of 1064±20 nm to 2500±20 nm, with a spectral width of about 5 nm, a forward current of about 1500 milliamps, and a forward voltage of about 5 volts at the maximum current.

In operation, the switch 20 is closed (i.e., turned on) to power up the control unit 12, at which time the displays becomes illuminated, thereby indicating that the control unit is receiving power. The time control 28 is set for specifying a desired duration of time for laser treatment, which time is displayed on the countdown display 36a. The mode control 34 is set for specifying whether the laser light is to be generated in the continuous or the pulsed mode. If the pulsed mode is selected, then the duration of the pulse on-time/off-time is specified and the pulses-per-second (and the pulse duty cycle if appropriate) is displayed on the PPS display 40*a*. If the continuous mode instead is chosen, the continuous mode display 40*b* is illuminated. It can be appreciated that the mode and the pulse time-on and time-off settings affect the intensity of the treatment provided. The amount of power is further set by the power control 30, and displayed on the power display 38. It can be appreciated that the power, duration and pulse intensity of treatment is is thus selectable by the unit 12 and is to be determined by treatment protocols relating to the character of the tissue to be treated, the depth of penetration desired, the acuteness of the injury, and the condition of the patient. The audio volume control 46 can be adjusted to control the volume of the tone generated from the speaker 48. The tissue impedance display 42 indicates an impedance value for tissue in contact with it and can be calibrated to a baseline set for the patient by applying the wand 14 to surrounding non-damaged tissue and then when the wand 14 is applied to the damaged tissue, an impedance value (much higher than the baseline) will be indicated and hopefully reduced over time, through treatment, to the baseline value.

After the time, power, and mode (continuous wattage or pulsed at a selected intensity) selections are made, the wand 14 may be directed into the calibration port 49 to verify the accuracy of the system. The wand 14 may then be applied to patient tissue for therapy, The foot pedal 22 and/or the switch 64 may be depressed to cause therapeutic laser light energy to be generated from the wand 14. As an indication of that laser light energy is being generated, an audible tone is generated from the speaker 32. In accordance with the foregoing specification of the laser diode 70, the laser light energy is generated at a fundamental wavelength of 1064 nm at an output power level of from about 100–800 mw. In other implementations the laser light wavelength may be as high as about 2500 nm and power of up to 1000 mw.

The generated laser optical energy is applied to regions of the body where decreased muscle spasms, increased circulation, decreased pain, or enhanced tissue healing is desired. The surface of the tissue in the region to be treated is demarcated to define an array of grid treatment points, each of which points identifies the location of an aforementioned small treatment area. Each small treatment area is irradiated with the laser beam light to produce the desired therapeutic effect. Because laser light is coherent, a variable energy density of the light of from about 0.01 to 0.15 joules/mm$^2$ is obtained as the light passes through the lens 74 and converges onto each of the small treatment areas. The energy of the optical radiation is controlled by the power control 30 and applied (for durations such as 1 minute to 3 minutes, continuous wattage or pulsed, for example) as determined by treatment protocols, to cause the amount of optical energy absorbed and converted to heat to be within a range bounded by a minimum absorption rate sufficient to elevate the average temperature of the irradiated tissue to a level which is above the basal body temperature, but which is less than the absorption rate at which tissue is converted into a collagenous substance. The laser beam wavelength, spot or beam size, power dissipation level, and time exposure are thus carefully controlled to produce in the irradiated tissue a noticeable warming effect which is also limited to avoid damaging the tissue from thermal effects.

The present invention has several advantages. For example, by using an In:GaAs diode laser to generate the laser beam energy, the laser source can be made sufficiently small to fit within the hand-held wand 14, thereby obviating the need for a larger, more expensive laser source and the fiber optic cable necessary to carry the laser energy to the treatment tissue. The In:GaAs diode laser can also produce greater laser energy at a higher power dissipation level than lasers of comparable size. Furthermore, construction of the wand 14 including the fins 58 provides for the dissipation from the wand of the heat generated by the laser source.

A further advantage is that therapeutic treatment by the foregoing low level reactive laser system has been shown to reduce pain in soft tissue, reduce inflammation, and enhance healing of damaged tissue by the stimulation of microcirculation, without subjecting the living tissue to damaging thermal effects. This phenomenon is due to certain physiological mechanisms in the tissue and at the cellular level that occur when the above process is used. In the evaluation of the microcirculatory system, for example, it has been demonstrated that the blood vessel walls possess photosensitivity. When the blood vessel walls are exposed to laser irradiation as set forth above, the tonus is inhibited in smooth myocytes, thus increasing the blood flow in the capillaries. Other effects which have been observed are: peripheral capillaries neovascularization, reduction of blood platelet aggregation, reduction of $O_2$ from the triplet to the singlet form which allows for greater oxygenation of the tissue, reduction of buffer substance concentration in the blood, stabilization of the indices of erythrocyte deformation, reduction of products of perioxidized lipid oxygenation of the blood. Other effects which have been observed are increased index of antithrombin activity, stimulation of the enzymes of the antioxidant system such as superoxide dismutase and catalase. An increase in the venous and lymph and outflow from the irradiated region has been observed. The tissue permeability in the area is substantially enhanced. This assists in the immediate reduction of edema and hematoma concentrations in the tissue. At the cellular level, the mitochondria have also been noted to produce increased amounts of ADP with subsequent increase in ATP. There also appears to be an increased stimulation of the calcium and sodium pumps at the tissue membrane at the cellular level.

At the neuronal level, the following effects have been observed as a result of the foregoing therapeutic treatment. First, there is an increased action potential of crushed and intact nerves. The blood supply and the number of axons is increased in the irradiated area. Inhibition of scar tissue is noticed when tissue is lazed. There is an immediate increase in the membrane permeability of the nerve. Long term changes in the permeability of calcium and potassium ions through the nerve for at least 120 days have been observed. The RNA and subsequent DNA production is enhanced. Singlet $O_2$ is produced which is an important factor in cell regeneration. Pathological degeneration with nerve injury is changed to regeneration. Both astrocytes and oligodedrocytes are stimulated which causes an increased production of peripheral nerve axons and myelin.

Phagocytosis of the blood cells is increased, thereby substantially reducing infection. There also appears to be a significant anti-inflammatory phenomena which provides a decrease in the inflammation of tendons, nerves, bursae in the joints, while at the same time yielding a strengthening of collagen. There is also an effect on the significant increase of granulation tissue in the closure of open wounds under limited circulation conditions.

Analgesia of the tissue has been observed in connection with a complex series of actions at the tissue level. At the local level, there is a reduction of inflammation, causing a reabsorption of exudates. Enkephalins and endorphins are recruited to modulate the pain production both at the spinal cord level and in the brain. The serotnogenic pathway is also recruited. While it is not completely understood, it is believed that the irradiation of the tissue causes the return of an energy balance at the cellular level which is the reason for the reduction of pain.

It is understood that several variations may be made in the foregoing without departing from the scope of the invention. For example, any number of fins 58 may be utilized as long they dissipate sufficient heat from the wand 14 so that the user may manipulate the wand without getting burned. The setting controls 24 may be used individually or in combination and the information displayed on the displays 26 may vary. Other diode laser structures may be utilized to produce the desired effects.

Although illustrative embodiments of the invention have been shown and described, a wide range of modification, change, and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. A diode laser cooling apparatus for cooling a diode laser used in a diode laser irradiation system for treating biological tissue of a subject without exposing the tissue to damaging thermal effects, the apparatus comprising:

a conductive bar for supporting the diode laser at one end thereof;

an insulative sleeve over the bar; and a plurality of cooling fins connected to an opposite end of the bar for transferring heat generated by the diode laser to the surrounding air.

2. A manipulable wand for use in a diode laser irradiation system for treating biological tissue of a subject without exposing the tissue to damaging thermal effects, comprising:

a diode laser for irradiating the tissue with coherent optical energy at a predetermined power output level focused to an area in the range of about 0.5 $mm^2$ to about 2 $mm^2$;

a conductive bar for supporting the diode laser at one end thereof;

an insulative sleeve over the bar; and a cooling fin connected to the bar for transferring heat generated by the diode laser to the surrounding air.

3. The wand of claim 2 wherein the predetermined power output level is less than one thousand milliwatts.

* * * * *